United States Patent [19]

Cannon

[11] 4,412,819

[45] Nov. 1, 1983

[54] ORTHODONTIC ARCH WIRE

[76] Inventor: James L. Cannon, Rte. 2, Dahlonega, Ga. 30533

[21] Appl. No.: 418,259

[22] Filed: Sep. 15, 1982

[51] Int. Cl.³ .............................................. A61C 7/00
[52] U.S. Cl. .................................................... 433/20
[58] Field of Search ..................................... 433/7, 20

[56] References Cited

U.S. PATENT DOCUMENTS 1,938,428 12/1933 Johnson ................................ 433/20
2,318,001 5/1943 Linde .................................... 433/7

*Primary Examiner*—Robert Peshock
*Attorney, Agent, or Firm*—Christie, Parker & Hale

[57] ABSTRACT

An orthodontic arch wire having anterior and posterior segments of different elasticity or stiffness to enable early and simultaneous treatment of teeth in the entire dental arch. The wire is preferably made by uniting a central segment of relatively resilient wire with end or posterior segments of a different and more rigid wire. Different cross-sectional shapes may also be used in the several segments.

14 Claims, 5 Drawing Figures

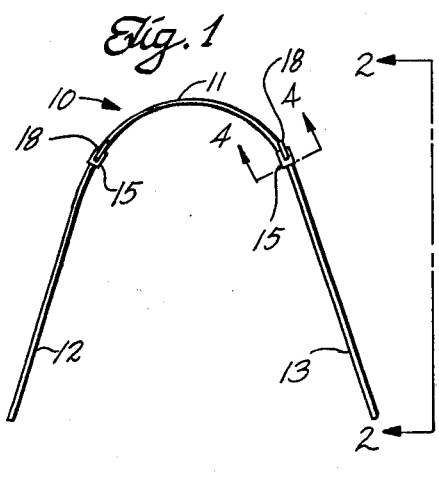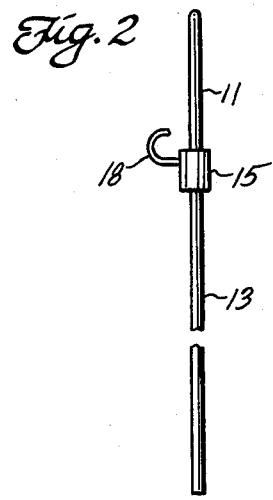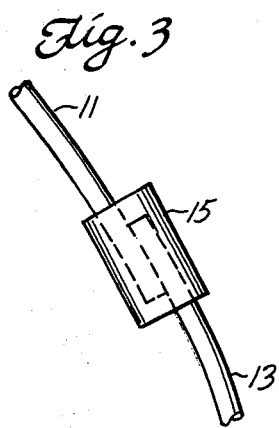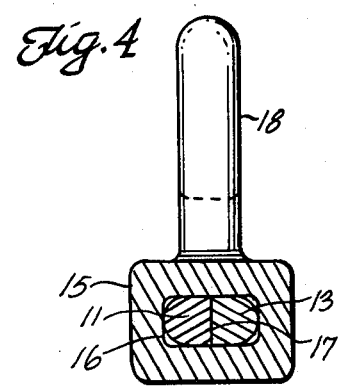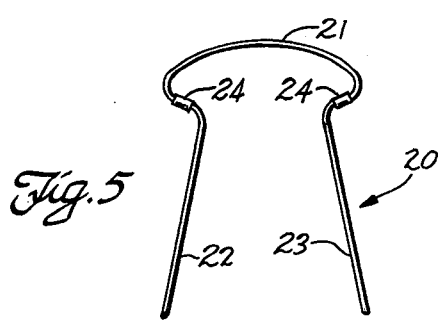

ORTHODONTIC ARCH WIRE

BACKGROUND OF THE INVENTION

Orthodontics is a specialized dental practice concerned with the movement of teeth to achieve an effective occlusion (the proper mating of the upper and lower teeth), and to provide a pleasing facial contour and appearance of the teeth. Tooth movement is accomplished by applying a force to the tooth in the direction of desired movement. A relatively long-term application of corrective force of the proper level will cause the tooth root to move within the supporting bone (the upper and lower jawbones, respectively the maxilla and mandible) to enable tipping, rotation, translation, and other tooth movements needed to align maloccluded dental arches.

Corrective force is provided by the restoring force exerted by a stressed or activated elastic element such as flexible metal wire, a metal spring, or a band such as a "rubber" band made of a material compatible with the mouth environment. The most common and useful elastic element in modern orthodontics is a metal arch wire of roughly U-shape to conform to the array of teeth in each dental arch. The arch wire is coupled to the teeth by slotted orthodontic brackets secured to the teeth either by direct adhesive attachment, or by being fastened to a tooth band fitted over and cemented to the teeth. The arch wire is distorted or flexed when fitted into the bracket slots, and the resulting restoring force is exerted through the brackets on the teeth to urge them into proper alignment.

Critical factors in orthodontic treatment include the selection and placement of orthodontic brackets, and the contouring of the arch wire. The combination of these factors determines the direction and level of corrective force applied to each tooth. Control of direction is essential to insure that each tooth is urged toward a position of proper alignment. Control of force level is equally important, both for patient comfort, and because excessive force will interfere with and impede the bone resorption process which enables the individual tooth roots to move slowly within the supporting bone.

Control of corrective force is complicated by the fact that the optimum force differs from tooth to tooth (depending on the size and engagement of the root structure), and also somewhat with the direction of desired movement. This factor has led to a somewhat serial approach to movement of individual groups of adjacent teeth, and overall treatment time is relatively long. Any reduction in overall treatment time is desirable out of consideration for patient comfort and appearance, and because in some cases it can reduce the expense of treatment.

Perhaps the most common malocclusion problems diagnosed by orthodontists prior to corrective treatment involve crowded and irregularly positioned anterior or front teeth (the central and lateral incisors) in either or both arches, and a closed bite or so-called Class II malocclusion where the upper maxillary front teeth are excessively far forward of the mating lower mandibular front teeth. Both problems interfere with chewing function and cosmetic appearance of the teeth, and the closed-bite factor is often manifested as an undesirable chin contour.

Preliminary alignment or "unraveling" of the relatively small anterior teeth requires application of light corrective force, whereas initial correction of a closed bite requires heavier forces to reposition the more massive posterior teeth (molars and bicuspids) which have larger root structures. With known arch wires, these demands are incompatible in that a small and limber arch wire is needed for bracket engagement on the badly misaligned front teeth, whereas a heavier and more rigid wire is needed for correction of the closed bite.

The result is that initial alignment is typically done in several serial-order stages, using a light wire for anterior alignment, and a heavier wire for subsequent posterior movement. This approach lengthens overall treatment time to the detriment of the patient. Perhaps the best prior-art solution to the problem is provided in the Begg light-wire technique which in effect decreases the stiffness of the anterior part of the arch wire by forming a series of stress-relieving loops in the wire portion spanning the front teeth. Such looped arch wires have shortcomings, however, in that it is difficult to avoid loop impingement on gingival or lip tissue, more frequent arch-wire replacement is required as the treatment program progresses, and the loops interfere with oral hygiene and gum massage during brushing by the patient.

The arch wire of this invention overcomes these problems by providing segments of differing stiffness or flexural rigidity along the length of the wire. The individual segments are united to form a fuctionally integral arch wire which enables control of and application of different forces to the different groups of teeth undergoing treatment. This enables preliminary treatment to proceed in simultaneously executed parallel stages for a significant reduction in overall treatment time. The new arch wire is useful with both light-wire and conventional edgewise orthodontic brackets, and can be used as a conventionally contoured wire, or with brackets configured for newer straight-wire or lingual techniques.

SUMMARY OF THE INVENTION

Briefly stated, this invention contemplates a composite arch wire having elongated anterior and posterior segments made of materials having different flexural rigidity or stiffness, with the anterior segment being more limber or flexible than the posterior segments. The segments are joined or united by crimped tubes, welding, brazing, soldering, or any other technique compatible with the metal alloys forming the several segments. A crimped-tube attachment is especially useful with an anterior segment made of Nitinol alloy which cannot be readily welded, and the tube also provides a base for an optional hook serving as a forward anchor for intraoral elastics.

DESCRIPTION OF THE DRAWINGS

FIG. 1 is a plan view of a composite arch wire according to the invention;

FIG. 2 is an enlarged side view on line 2—2 of FIG. 1;

FIG. 3 is an enlarged plan view of a crimpable tube for securing together the segments of the arch wire;

FIG. 4 is an enlarged sectional view on line 4—4 of FIG. 1 and showing a crimpable tube with an elastic hook; and FIG. 5 is a plan view of another form of composite arch wire useful with lingually positioned orthodontic brackets.

DESCRIPTION OF THE PREFERRED EMBODIMENT

A composite orthodontic arch wire 10 according to the invention is shown in FIGS. 1 and 2, and includes an anterior segment 11, and a pair of posterior segments 12 and 13 secured to and extending from the respective ends of the anterior segment. The anterior segment is made of a material having a stiffness or flexural rigidity which is less than that of the material forming the posterior segments. Flexural rigidity is used herein in a conventional sense as defined by Young's modulus of the segment times the second moment of inertia of the segment cross section. A helpful further discussion of arch-wire stiffness is provided by Waters et al., in the American Journal of Orthodontics, April 1981, at pp. 373–89.

The segments can be secured together by using any of several different attachment techniques. In the form shown in FIGS. 1 and 2, a crimpable metal tube 15 is provided at each segment junction for mechanical attachment of the segments. Tube 15 is shown in greater detail in FIGS. 3 and 4, and is a short length (typically about 0.080 inch) of generally rectangular cross-section stainless-steel tube with an internal bore 16 which is dimensioned to make a snug-fitting socket for the juxtaposed ends of overlapped segments 11 and 12 or 11 and 13. The segment lengths and tube positioning are usually selected to place the tubes just mesial of the cuspids when installed so the limber anterior segment spans the incisors.

Preferably, and as shown in FIG. 4, contacting faces 17 of the segments being joined are flattened (by swaging or grinding) to key the segments together against relative rotation. After the arch-wire segments are inserted in tube 15 (FIGS. 3 and 4), the tube is crimped labiolingually with a plier to deform the tube sidewalls, and thereby to secure the segments tightly together. In many cases, it is desirable to mount (by soldering or welding) a hook 18 (omitted in FIG. 3 for clarity) on the tube to provide a forward anchor for an intraoral elastic useful in correcting the aforementioned closed-bite condition. The hook is normally oriented to extend gingivally from the tube, and to open mesially when the arch wire is installed. The tube thus serves both as a joining member to unite the arch-wire segments, and as a base for an elastic hook.

Depending on the metal alloys used in the arch-wire segments, soldering, brazing, or welding may also be used to secure the segments together. To form a secure bond, the segments are preferably overlapped just as shown in FIG. 3 (but without tube 15 in place), and then secured together by, e.g., resistance welding. As discussed below, not all arch-wire metal alloys are suitable for welding, and the alternative attachment method using tube 15 will sometimes be the proper choice.

In a presently preferred form, anterior segment 11 is made of a nickel-titanium alloy known as Nitinol (available for arch-wire use from Unitek Corporation, Monrovia, Calif.). Segments formed from this alloy are very limber and resilient, and hence have the desired low flexural rigidity to enable bracket engagement, and for application of light corrective forces needed in the alignment of often badly malpositioned anterior teeth. Nitinol cannot be welded, and the segment-attachment method using tube 15 is accordingly recommended.

Other relatively limber wires can be used in the anterior segment which may be of either round or rectangular cross section. For example, a beta-titanium alloy which can be welded may be selected for this segment.

The greater stiffness needed in the posterior segments of the arch wire is provided by selecting one of the relatively rigid or stiff stainless-steel alloys (e.g. high-tensile alloys in the 302 or 304 series) which are commercially available from orthodontic suppliers. The posterior segments may be of either rectangular or round cross section, depending on the nature of the treatment program. The two posterior segments may also be of different cross section to accommodate the needs of a specific patient.

For example, space closure after a unilateral extraction (not accompanied by extraction of the corresponding tooth in the other quadrant of the dental arch) may be best accomplished using a round cross-section posterior segment bridging the extraction site in combination with Begg brackets, and an edgewise or rectangular cross-section posterior segment in the other quadrant. The posterior segments, without regard to cross section, are stiffer than the anterior segment, and have sufficient rigidity to permit formation of tipback bends, and to enable use of Class II elastics.

As shown in FIG. 1, composite arch wire 10 is of conventional generally U-shaped configuration for conformation with the patient's dental arch. The invention is equally useful with lingual brackets and related appliances which are mounted on the rear surfaces of the teeth. FIG. 5 shows a so-called "mushroom" arch wire 20 which is again of generally U-shaped configuration, but is contoured to conform to the curvature of the lingual or inner surfaces of the teeth. Arch wire 20 includes an anterior segment 21 of relatively low stiffness, a pair of posterior segments 22 and 23 of relatively higher stiffness, and crimped tubes 24 joining the segments and positioned to be just distal of the cuspids when installed.

Another typical application for the composite arch wire is as a "braking" arch wire which blocks or brakes retraction of now-aligned anterior teeth, while permitting forward movement of the posterior teeth to close extraction spaces left by extracted teeth which are typically bicuspids. A braking arch wire in the configuration of arch wire 10 is easily formed by combining a Nitinol anterior segment 11 (of say 0.018-inch square cross section) with more rigid posterior stainless-steel segments 12 and 13 (of say 0.018-inch circular cross section).

The exact choice of segment cross section and dimensions of the several segments will be determined by the treatment program planned by the orthodontist, but the anterior segment always has a flexural rigidity lower than that of at least one and more typically both of the posterior segments. The new composite arch wire provides significant benefits to both orthodontist and patient in terms of shortening treatment time, minimizing patient discomfort, and providing more precise control of tooth movement.

What is claimed is:

1. An orthodontic arch wire, comprising a generally U-shaped assembly of an elongated anterior segment, and a pair of spaced-apart elongated posterior segments secured to and extending from respective ends of the anterior segment, the anterior segment being made of a material having a flexural rigidity which is lower than the flexural rigidity of material forming at least one of the posterior segments.

2. The arch wire of claim 1 wherein the flexural rigidity of the anterior segment is lower than the flexural rigidity of both posterior segments.

3. The arch wire of claim 2 wherein the adjacent segments are overlapped and further comprising a crimpable tube at each segment junction and fitted over the overlapping segments to secure the segments together.

4. The arch wire of claim 3 wherein facing surfaces of the overlapping segments are flattened to resist relative rotation when the tube is crimped.

5. The arch wire of claim 4, and further comprising a hook member secured to and extending from each crimpable tube.

6. The arch wire of claim 3 wherein the anterior segment is dimensioned to span the central and lateral incisor teeth when installed, and the crimpable tubes are positioned distally of the incisor teeth.

7. The arch wire of claim 2 wherein the segments are secured together by welding.

8. The arch wire of claim 2 wherein the posterior segments have the same flexural rigidity.

9. The arch wire of claim 2 wherein the posterior segments have different flexural rigidities.

10. The arch wire of claim 2 wherein each segment is a single metal strand.

11. The arch wire of claim 10 wherein the anterior segment is a titanium alloy.

12. The arch wire of claim 11 wherein the anterior segment is made of Nitinol, and the posterior segments are made of stainless steel.

13. The arch wire of claim 10 wherein the anterior and posterior segments have the same cross-sectional shape.

14. The arch wire of claim 10 wherein the anterior segment has a cross-sectional shape differing from the cross-sectional shape of at least one of the posterior segments.

* * * * *